United States Patent [19]
Bailey et al.

[11] 4,289,853
[45] * Sep. 15, 1981

[54] HIGH LOADING OF IMMOBILIZED ENZYMES ON ACTIVATED CARBON SUPPORTS

[75] Inventors: James E. Bailey, Houston, Tex.; Yong K. Cho, Rockford, Ill.

[73] Assignee: Illinois Water Treatment Company, Rockford, Ill.

[*] Notice: The portion of the term of this patent subsequent to May 20, 1997, has been disclaimed.

[21] Appl. No.: 147,353

[22] Filed: May 7, 1980

Related U.S. Application Data

[62] Division of Ser. No. 838,544, Oct. 3, 1977, Pat. No. 4,204,041.

[51] Int. Cl.³ .............................................. C12N 11/02
[52] U.S. Cl. ................................... 435/177; 435/174
[58] Field of Search ............... 435/174, 177, 178, 180, 435/181

[56] References Cited

U.S. PATENT DOCUMENTS 3,919,048  11/1975  Dahlmans et al. ............... 435/177
4,204,041   5/1980  Bailey et al. ..................... 435/177

OTHER PUBLICATIONS

Zaborsky, O., Immobilized Enzymes, CRC Press, Cleveland, Ohio, 1973, (pp. 5-9, 24 & 25).
Liu, et al., Immobilization of Lactase on Carbon, Biotech. and Bioeng., vol. XVII, 1957, (pp. 1695-1696).
Line, et al., Pepsin Insolubilized by Covalent Attachment to Glass, Biochim. Biophys. vol. 242, 1971, (pp. 194-202).

*Primary Examiner*—David M. Naff
*Attorney, Agent, or Firm*—Mason, Kolehmainen, Rathburn & Wyss

[57] ABSTRACT

Enzymes are immobilized on activated carbon supports at high load levels and with high stability by reacting an activated carbon support with a carbodiimide or an isoxazolium salt to form active organic radicals on the surface of the activated carbon support and thereafter treating the carbon support with an enzyme solution to immobilize the enzyme on the carbon support. The immobilization of enzymes on activated carbon provides immobilized enzymes which are easily handled and which are stabilized against denaturation by hydrogen peroxide.

4 Claims, 3 Drawing Figures

HIGH LOADING OF IMMOBILIZED ENZYMES ON ACTIVATED CARBON SUPPORTS

This is a division of application Ser. No. 838,544, filed Oct. 3, 1977, now U.S. Pat. No. 4,204,041.

FIELD OF THE INVENTION

This invention relates to a process for immobilizing an enzyme on an activated carbon support and to products obtained thereby.

DESCRIPTION OF THE PRIOR ART

It has long been known that enzymes and other proteinaceous molecules can be immobilized onto various supports such that the immobilized protein retains its activity to at least some useable degree. The immobilized configuration is especially desirable for ease of storage, handling and operation (e.g., flow-through systems using columns may be used) and because it enables the efficient reuse of the enzyme. Moreover, in general, the stability of an immobilized enzyme is increased over the normal watersoluble form.

Conventionally, enzymes have been immobilized on both organic (e.g., polymeric supports such as DEAE-cellulose, polystyrene, etc.) and inorganic (e.g., porous glass, silica, alumina, activated carbon) supports by a variety of techniques. For example, the enzymes can be attached directly to substrates, as disclosed in U.S. Pat. No. 3,919,048 and in Line et al, *Biochem. Biophys. Acta.*, 242, 194–202 (1971) where a carbodiimide is applied to a sponge or a porous glass substrate. Thereafter, a carboxyl group from an enzyme forms an amide linkage with the carbodiimide, directly connecting the enzyme to the substrate. Alternatively, intermediate bridging agents can be used to covalently couple the enzyme to the support, as shown in U.S. Pat. No. 3,930,951, where bridging diazo compounds are used to immobilize enzymes onto porous glass or metal oxide substrates. In another procedure, the enzyme may first be adsorbed onto the substrate and then "fixed" by addition of a crosslinking agent, which forms covalent bridges between adjacent enzyme molecules. In this mode, the enzyme forms a net-like structure around the substrate. This technique is described, for example, in U.S. Pat. Nos. 3,804,719 and 3,796,634.

A particularly attractive substrate for enzyme or other protein immobilization is activated carbon. This material is readily available, relatively inexpensive, highly stable, of good mechanical strength and obtainable with a wide variety of pore size distributions and particle sizes. Moreover, activated carbon possesses many surface functional groups which are readily available for enzyme immobilization (e.g., carboxyl, hydroxyl, carbonyl and like substituents). Heretofore, the amount of enzyme which could be loaded onto an activated carbon support has been quite low, i.e., less than the loadings (milligrams of immobilized enzyme per gram of support) obtainable with other substrates such as porous glass or cellulosic materials. For example, less than 1 mg/g of lactase has been successfully loaded on an activated carbon support with a glutaraldehyde cross-linking agent. (Liu et al, *Biotechnol. Bioeng.*, 17, 1695 (1975); Stoner et al, *Biotechnol. Bioeng.*, 17, 455 (1975)). Moreover, the stability, i.e., resistance to denaturation, of enzymes immobilized on an activated carbon substrate has also been inferior to that observed for a number of other conventional substrates.

In addition, unlike most other conventional supports, activated carbon is a useful catalyst in and of itself. Unfortunately, in the conventional enzyme immobilization techniques so far used with activated carbon, the support loses most if not all of its catalytic activity. Simultaneously, it loses its capacity as an adsorbent substrate for molecules other than the already immobilized enzymes.

Consequently, it would be most desirable to have a procedure for immobilizing enzymes on activated carbon support wherein high loadings of enzyme and high enzyme stability are achieved. In addition, it would also be desirable to obtain, as a result of such a process, an activated carbon support, having enzyme immobilized thereon, which retains its own catalytic and adsorbent properties.

SUMMARY OF THE INVENTION

Accordingly, it is one object of the present invention to provide a method of immobilizing an enzyme on an activated carbon support which achieves high enzyme loadings and results in highly stable immobilized enzymes.

It is another object of this invention to provide such a procedure wherein the activated carbon support simultaneously retains its catalytic and adsorbent properties.

It is still another object of this invention to provide an activated carbon substrate, highly loaded with a stable immobilized enzyme, which combination displays both enzymatic catalytic behavior and the catalytic and/or adsorbent behavior of activated carbon.

A further object is to provide a procedure of immobilizing an enzyme on activated carbon by reacting said carbon with a water-soluble carbodiimide and thereafter treating said carbon with an enzyme.

These and other objects of this invention, which will hereinafter become clear, have been attained by providing an enzyme immobilization procedure which comprises contacting an activated carbon support with a solution of a carbodiimide and thereafter loading the enzyme thereupon.

BRIEF DESCRIPTION OF THE DRAWINGS

A more complete understanding of the invention and many of the attendant advantages thereof will be readily attained as the same becomes better understood by reference to the following detailed description when considered in connection with the accompanying drawings, wherein.

BACKGROUND OF THE INVENTION

Figure 1:
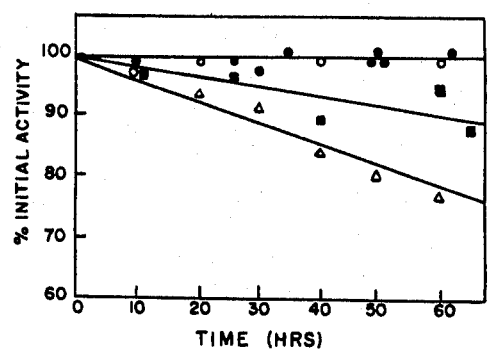
FIG. 1 illustrates the storage stability of enzymes immobilized on carbon in accordance with this invention and by conventional procedures.

In a situation apparently peculiar to biological catalysis, the enzyme glucose oxidase catalyzes the production of hydrogen peroxide, a powerful agent for destruction of enzyme activity. Catalase, which is a common impurity in many glucose oxidase preparations, ameliorates peroxide attack on the oxidase by catalyzing peroxide decomposition, and in fact has been added to glucose oxidase preparations in an attempt to extend their useful lifetimes. This approach has not generally succeeded because catalase itself is very susceptible to deactivation by hydrogen peroxide.

In a previous study aimed at an in vitro enzymatic process for producing gluconates from polysaccharides, glucoamylase deactivation caused by peroxide was observed. Some enhancement of glucoamylase longevity was obtained by addition of small amounts of a hydrogen peroxide stabilizing agent to the reaction mixture, but even with this protection only 25% of the initial glucoamylase activity remained after storage for 10 days at 30° C. in a 3.5 wt% $H_2O_2$ solution.

Another class of possible remedies for peroxideinduced deactivation includes nonenzymatic methods for $H_2O_2$ decomposition. Among these are decomposition by radiation, either by photochemical or radiochemical processes, electrolytic decomposition, and decomposition by nonenzymatic catalysts. Since the first two of these approaches involve substantial inputs of energy and may themselves reduce enzyme activity, it seems logical to focus on nonenzymatic catalysts for peroxide decomposition.

Of special interest in this regard is activated carbon. Besides catalyzing peroxide decomposition, activated carbon may be formulated with very high surface areas (600–1000 $m^2/g$) and a significant fraction (10–30%) of its pore volume in the 300–1000 Å range suitable for enzyme immobilization. Thus, the morphology of activated carbon is conducive to large loadings of immobilized enzyme. However, only a few previous studies of enzyme immobilization on activated carbon have been reported—immobilization of enzymes by adsorption and immobilization of lactase using glutaraldehyde cross-linking.

One motivation for attaching enzymes to a support which also destroys peroxide arises from the mass transfer limitations often observed in active, porous immobilized enzyme systems. Because of diffusional limitations, concentration gradients arise within the porous enzyme particle. Substrate and product concentrations at the center of the particle are smaller and greater, respectively, than these concentrations in the surrounding fluid. Therefore, with glucose oxidase immobilized on an inert support, enzyme deactivation will be most serious inside the particle where the greatest peroxide concentrations will exist. If, on the other hand, the glucose oxidase is immobilized on a very effective inorganic peroxide decomposition catalyst such as activated carbon peroxide will be decomposed within the porous particle as it is formed, and glucose oxidase deactivation will be alleviated.

GENERAL DESCRIPTION OF THE INVENTION

Broadly, this invention includes a procedure for immobilizing and stabilizing enzymes on porous particles of activated carbon and the products produced thereby. The procedure comprises contacting activated carbon with a solution of a carbodiimide or an isoxazolium salt to form a complex of carbon with the organic molecules. This complex is then contacted with an enzyme solution and the protein displaces the carbodiimide or isoxazolium salt, forming an enzyme-carbon complex with immobilized enzyme which is stabilized against deactivation and denaturation by peroxide.

The activated carbon can by any of the commercial activated carbons obtained from wood, nut shells, bone, coal, petroleum products and other plant sources. Among these are those sold under the names Darco G-60, Sigma, Nuchar, Norit, Aquadag and Carboraffin. Granular activated carbons marketed by Pittsburgh Activated Carbon Division of Calgon Corporation, Pittsburgh, under the symbols SGL, CAL, RB, and CPG are also operative. Other suitable forms and sources of activated carbons are described in "Active Carbon" by Smisek and Cerny, Elsevier Publishing Co., Amsterdam, 1970. The active carbon generally has particle sizes of from 300 to 1000 microns and surface areas of 600 to 1000 square meters per gram with 10–30% of its pore volume in pores of 300 to 1000 Å size. In a preferred form of activated carbon pores of 300 Å or larger constitute 25–30% of the total pore volume.

Use of activated carbon as an enzyme support combined with covalent enzyme immobilization substantially reduces the susceptibility of the bound enzyme to deactivation by hydrogen peroxide. Since the peroxide concentration encountered in an enzyme process for gluconate production is substantially less than the 500 mM level considered in these examples, deactivation will also be slower, possibly making the in vitro enzyme process economically viable.

Besides the peroxide protection afforded by an activated carbon enzyme support, this material is very promising in several other respects. Activated carbon possesses a mechanical strength comparable to porous glass materials, and enzyme loadings achieved here on activated carbon are very similar to those obtained on porous glass. Like porous glass, activated carbon can be fabricated with a variety of pore size distributions.

Further, activated carbon has several features which are not shared by porous glass materials. Pre-eminent in this regard are the relative prices; activated carbon being only 1/60th the price of porous glass. The skeletal density of activated carbon is 2.1 $g/cm^3$ contrasted to roughly 2.6 $g/cm^3$ for glass. This means that activated carbon immobilized enzymes can be fluidized or suspended in a slurry reactor much easier than enzymes supported on porous glass. Finally, activated carbon is a well-known and widely applied adsorbent for removal of trace impurities from liquids. Activated carbon enzyme supports can therefore protect enzymes from poisoning by trace metals or other impurities in complex industrial process mixtures by adsorbing these impurities before they can penetrate to the interior of the porous pellet.

In one modification of the invention, the activated carbon is oxidized before it is treated with enzyme. Generally this is done with dilute nitric acid at ambient temperature. It has been found that such treatment increases the loading capacity of the carbon substrate, allowing it to immobilize larger amounts of enzyme than ordinarily.

DETAILED DESCRIPTION OF THE INVENTION

The enzymes which can be immobilized by the procedure of this application include any of the known enzymes. The most important enzyme groups with respect to this invention are the hydrolases, particularly the glycosidases, the tranferases and the oxidases. Specific enzymes which are operative include α-glucosidase, glucoamylase, glucose oxidase, papain, trypsin, lactase, glucose isomerase, amylase, maltase, urease, urease, etc.

The immobilizing agent is preferably a carbodiimide or an isoxazolium salt. Among the carbodiimides are dicyclohexylcarbodiimide, dibenzylcarbodiimide, 1-cyclohexyl-3-(2-morpholinoethyl)carbodiimide, 1-benzyl-3-(2-diethylaminoethyl)carbodiimide, 1-cyclohexyl-3-(2-morpholinoethyl)carbodiimide metho-p-toluenesulfonate, 1-cyclohexyl-3-(2-morpholinoethyl)carbodiimide methochloride or methobromide and 1-(3-dimethylaminopropyl)-3-ethylcarbodiimide. The first four carbodiimides listed above are insoluble in water and are used in organic solvents such as tetrahydrofuran, methylene chloride or acetonitrile. The third and fourth carbodiimides are soluble in dilute aqueous acid and the last four carbodiimides are in the form of quaternary ammonium salts which are soluble in water.

The carbodiimides are believed to couple with carboxyl radicals on the surface of the activated carbon. Then the enzyme, through an amino radical, interacts with the active intermediates formed by the coupling reaction, displaces the derivatives of carbodiimide and forms a peptide bond. This mechanism can be illustrated by the following equations:

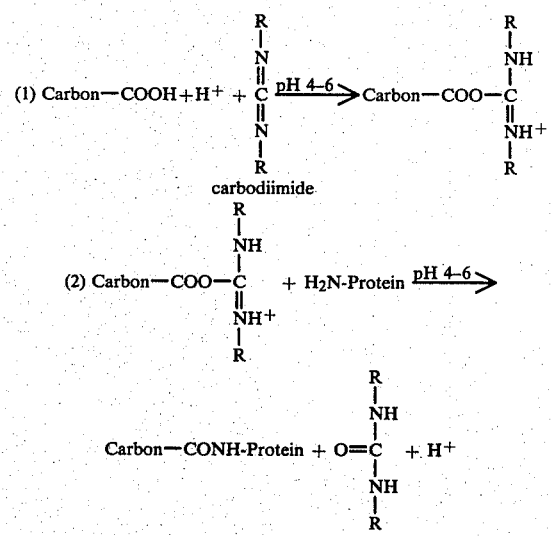

The carbon-carbodiimide-protein reaction can be run in inert organic solvents or in dilute aqueous acid (pH 4-6). When water is the solvent it is desirable to use a carbodiimide which is soluble in dilute aqueous acid; the urea derivative which is formed will also be soluble in water and thus simplify purification of the carbon-enzyme product.

Besides attractive loading characteristics, enzymes immobilized on activated carbon via the diimide procedure show excellent stability (i.e., resistance to denaturation). FIG. 1 compares the deterioration of glucoamylase and glucose oxidase activity under storage at 30° C. for different immobilization methods. Only the diimide [1-cyclohexyl-3-(2-morpholinoethyl)carbodiimide metho-p-toluenesulfonate] preparation shows negligible activity loss.

Figure 2:
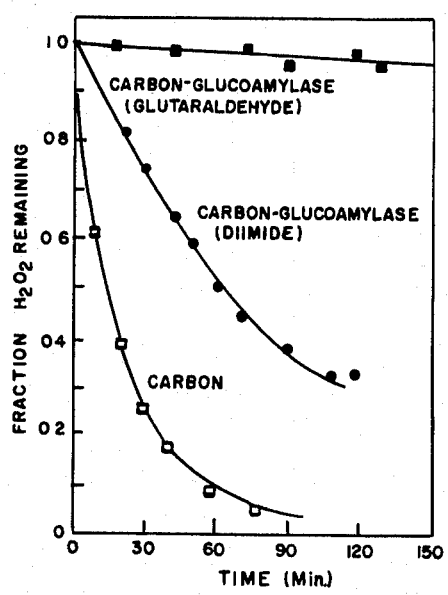
FIG. 2 displays carbon substrate activity after enzymes have been immobilized both by conventional procedures and that of this invention.

Activated carbon is an active catalyst for hydrogen peroxide decomposition (see curve marked "Carbon" in FIG. 2). Substantial peroxide decomposition catalytic activity of the carbon remains after enzymes have been immobilized by the procedure of this application (middle curve, FIG. 2) whereas enzyme immobilization on carbon by glutaraldehyde crosslinking (C. C. Liu et al, *Biotech. & Boengr.*, 17, 1695 (1975)) greatly inhibits the peroxide decomposition by the carbon (upper curve, FIG. 2).

Figure 3:
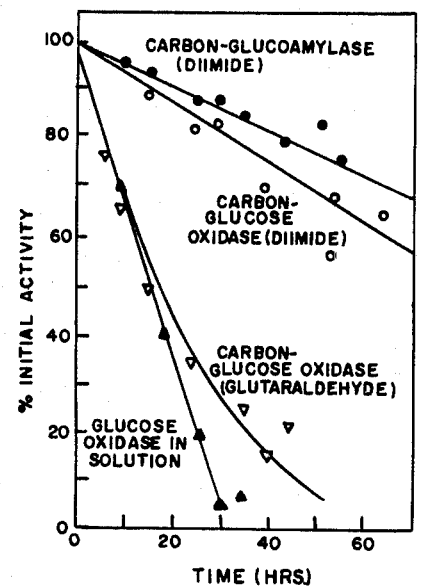
FIG. 3 shows the lifetime conditions under reaction of immobilized enzymes made by both conventional procedures and that of this invention.

This result is extremely important because (i) hydrogen peroxide is produced in many oxidations catalyzed by enzymes and (ii) hydrogen peroxide causes rapid deactivation of many enzymes. Thus, enzymes immobilized on activated carbon by the procedures of this application exhibit greatly extended lifetimes in the presence of hydrogen peroxide and/or biological oxidation reactions. The data represented in FIG. 3 show activity loss of activated carbon-glucose oxidase (diimide coupled) in a continuous flow vessel which is constantly fed with 500 mM $H_2O_2$ solution. For example, in an immobilized enzyme process for gluconate production from glucose, glucose oxidase immobilized on carbon would remain active for a much longer period than on other supports because the peroxide formed during glucose oxidation would be rapidly decomposed within the porous carbon pellet.

In more general terms, this invention represents the first in which enzymes (biological catalysts) have been immobilized on the surface of a nonbiological catalyst with an improved process as the result.

Activated carbon is an effective adsorbent for many ions, metals, and gases. There are situations in which intimate combination of enzyme catalytic activity and activated carbon adsorption will be valuable. For example, longer enzyme lifetimes may be obtained because the carbon adsorbs trace solutes which would otherwise deactivate the enzyme. Artificial kidney devices have been proposed in which activated carbon is placed in a chamber with pellets carrying immobilized urease, with the carbon function one of removing ammonium ions produced by urea decomposition. This process would function better if the ammonium ions are adsorbed on the enzyme support itself before escaping into the surrounding bulk liquid.

In addition to the carbodiimide immobilizing agents, this invention includes isoxazolium salts as such agents. These salts are zwitterions of the general formula

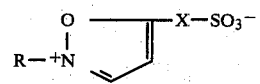

wherein R is a lower alkyl radical and X is a bivalent lower alkylene or arylene radical. The most common of such salts is known as Woodward's reagent K and is described by Woodward et al in *J.Am. Chem. Soc.*, 83, 1010-1012 (1961). In reagent K, R is ethyl and X is phenylene. These salts form active esters with activated carbon which, on treatment with a solution of an enzyme, form carbon-enzyme complexes in which the enzyme is immobilized and stabilized.

The invention is disclosed in further detail by the following examples which are provided for purposes of illustration. It will be apparent from the disclosure to those skilled in the art that various modifications can be made in materials and operating conditions without departing from the invention as herein described.

EXAMPLE 1

Active groups (—COOH and —OH) on the surface of activated carbon particles are activated either by a water soluble 1-cyclohexyl-3-(2-morpholinoethyl) carbodiimide quaternary ammonium salt (CMC quaternary ammonium salt) or by 1-(3-dimethylaminopropyl)-3- ethylcarbodiimide (DEC). The resulting active intermediate is used for enzyme immobilization.

CARBON PREPARATION

Activated carbon obtained from a commercial source (Pittsburgh Carbon Co.) is sized to 450–680 μm particles. 50 grams of the particles are mixed with 400 ml of deionized water in a 600 ml beaker. The slurry is agitated with marine-type impellor (diameter approx. 4–5 cm) for 5 to 10 minutes. This washing is continued with change of solution every 5 to 10 minutes until a clear solution is obtained. These particles are then treated with 400 ml of 1-N HCl at 50° to 60° C. for 12 hours with agitation. The pellets are rinsed well with warm deionized water until no chloride ions are detected. As an alternative to measuring choloride ion, water conductivity can be monitored until the conductivity of the bulk solution is below 20 micromhos/cm. The carbon pellets are dried at 100° C. overnight and stored under vacuum (10–15 psig) at room temperature until immobilization is conducted.

IMMOBILIZATION

One gram of the above carbon is mixed with 5 ml of deionized water in a 50 ml beaker. After gentle shaking, the supernatant liquid is carefully pipetted to remove as much accompanying carbon powder as possible. To this slurry 2 ml of 0.1 M CMC metho-p-toluenesulfonate in pH 5.2 buffer solution (0.01 M NaOH-HCl buffer) or 2 ml of 0.1 M DEC in the same buffer, which is prepared prior to the immobilization, is added with gentle shaking for the activation. After the slurry is left over 15 minutes at room temperature, as much liquid as possible is removed with a pipette. The cake is briefly rinsed once with 10 ml of the same buffer by addition along the wall of the container. The immobilization is commenced immediately by adding 30–100 mg protein in 3–15 mls. of the same buffer. The immobilization is carried out at room temperature for 24 hours under the covered container. During the first 2 to 3 hours of immobilization the pH of the bulk solution should be adjusted to pH 5.2 with 0.1-N NaOH solution.

The immobilized slurry is rinsed 5 times with 20 ml of cold (10° C.) deionized water. The cake is stored at 0°–5° C.

EXAMPLE 2

This example illustrates the prior oxidation of activated carbon followed by diimide immobilization. The procedure is the same as Example 1, except the acid-treated carbon divided into three equal portions and each portion (20 g) is treated with one of the following oxidizing agents:

(a) 2 g KMnO4 in 200 ml of 3 N-NaOH at 70° C. for 30 minutes (b) Mixed acid (equal volume of 100% of $H_2SO_4$ and $HNO_3$) for 1 hour at 30° C.; 200 ml of mixed acid for 20 gm. of support (c) 200 ml of 70% $HNO_3$ for 2 hours at 60° C. After each treatment, 20 grams of the carbon are rinsed as follows:

For KMnO4 oxidized carbon, 150 ml of 1% NaOH solution is stirred with the pellets at 40° to 59° C. for 2 to 3 hours. This step is repeated 3 times with fresh solution or until no brown to yellowish color is observed. Final washing is done with the same volume of deionized water until the solution conductivity is below 20 micromhos/mm at room temperature.

For acid treated carbon, the above step using 1% NaOH solution is omitted. Otherwise, the same washing procedure is conducted. The carbon is dried overnight at 100° C. and stored in a desiccator under vacuum (10–15 psig) until ready for immobilization. The well-washed and dried carbon is then employed for diimide coupling as described in Example 1.

The table below summarizes some of the loadings obtained by the methods of these examples.

| Enzyme Loadings on Activated Carbon via Diimide Coupling (mg.protein/gm. carbon) | | |
|---|---|---|
| | Example 1 | Example 2 |
| Glucoamylase | 27–33 | 15–50 |
| Glucose oxidase | 30–63 | |

These compare very favorably with reported loadings of 24 mg/gm and 25 mg/gm for these enzymes on the same size of polystyrene and porous glass, respectively.

EXAMPLE 3

This example illustrates enzyme immobilization procedures with several activated carbon pretreatment methods. In all these procedures the diimide was 1-cyclohexyl-3-(2-morpholinoethyl)carbodiimide metho-p-toluenesulfonate. The most important data are those which give the observed catalytic activity of the different immobilized enzyme preparations. These are stated in terms of the rate of formation of glucose resulting from maltose hydrolysis on a per gram of carbon basis. The data on hydrogen peroxide decomposition give the time required for half of an initial charge of hydrogen peroxide to be decomposed. Thus, for these data, smaller numbers indicate greater activities. The set of half times given in parentheses for each preparation (along with the half times for carbon with adsorbed enzyme) are for the carbon preparations after pretreatment but before enzyme immobilization.

The most important data to compare are results from the different pretreatment procedures employed with glutaraldehyde and diimide immobilization methods. The adsorption results are of less interest because in this case the enzyme tends to leach from the preparation with time. For example, after 36 hours, the various preparations immobilized by adsorption have lost from 16 to 22 percent of their initial activity. Similar activity losses are not observed for diimide preparations, however, until after 1 month. In a separate experiment not listed on the table, the diimide preparation was stored with constant agitation in a shaker bath at 30° C. for 1 month, and retained 80% of its activity after this time. Over a 36-hour period the small losses of activity for diimide and glutaraldehyde are quite similar.

IMMOBILIZATION PROCEDURES

Pittsburgh Activated Carbon SGL granular carbon was ground with a ball mill and sieved for 425–686μ-sizes. This grade of carbon, prior to ball milling, had the following characteristics:

| | |
|---|---|
| Total Surface Area, m$^2$/g | 950–1050 |
| Apparent Deensity (Bulk Density, dense packing), g/cc | 0.48 |
| Particle Density (Hg Displacement), g/cc | 0.75 |
| Real Density (He Displacement), g/cc | 2.1 |
| Pore Volume (Within Particle), cc/g | 0.85 |
| Voids in Dense Packed Column, % | 36 |

-continued

| | |
|---|---|
| Specific Heat at 100° C. | 0.25 |
| Mesh Size, U.S. Sieve Series | 8 × 30 |
| Larger than 8 mesh, Maximum, % | 15 |
| Smaller than 30 mesh, Maximum, % | 4 |
| Mean Particle Diameter, mm | 1.5–1.7 |
| Iodine Number, Minimum | 900 |
| Molasses Number, Minimum | 200 |
| Moisture as packed, Maximum, % | 2.0 |
| Abrasion Number, Minimum | 75 |
| Ash, Maximum | 10 |

The carbon particles were washed several times with dionized water until the washing solution remained clear and dried at 105° C. for 12 hours. The carbon was further treated or oxidized as below:

Preparation 1: The carbon obtained as above, with no further treatment.

Preparation 2: 20 grams of Preparation 1 were extracted in a Soxhlet apparatus with 1.25 liters of 1.7 N HCl for 48 hrs. at 75° C. The carbon was thoroughly washed with water until no chloride ions were detected.

Preparation 3: 10 grams of Preparation 1 were refluxed in 400 ml of 70% $HNO_3$ for 7 days at 50° C. The carbon was washed thoroughly with deionized water until no nitrate ions were detected.

Preparation 4: 20 grams of Preparation 2 were further oxidized with 200 ml of 5% $KMnO_4$ in 0.5 N NaOH for 12 hrs. at 25° C. The carbon was washed 3 times with 100 ml of hot water and 2 times with 50 ml of 18% HCl at 50° C. The oxidized carbon thus obtained was washed thoroughly in a shaker bath at 30° C. for 24 hrs. with frequent change of water or until no chloride ions were detected.

The four activated carbon preparations described above were loaded with glucoamylase by three procedures: (1) by direct adsorption of the enzyme on the carbon, (2) by the glutaraldehyde immobilization procedure of Liu et al, *Biotech. & Bioengr.*, 17, 1695 (1975) and (3) by the carbodiimide procedure of this application. The details on these procedures and the test results on the products are set forth in the following table:

well known, and has been employed before with activated carbon as well as numerous other insoluble supports. The second employs diimide-activated carboxyl and hydroxyl groups on the carbon surface to achieve covalent enzyme linkage to the support.

Five grams of the acid-washed carbon is mixed with 10–20 ml buffer (pH 4.6). To this slurry 250 mg of water soluble diimide (1-cyclohexyl-3-(2-morpholinoethyl)-carbodiimide metho-p-toluenesulfonate) is added with gentle shaking. Alternatively, 130 mg of 1-(3-Dimethylaminopropyl)-3-ethylcarbodiimide may be employed as the activating agent. After 5 to 10 minutes, from 150 to 500 mg of enzyme in the same buffer is added. The immobilization is carried out at room temperature for 24 hours.

For batch experiments a 500 ml Pyrex vessel agitated by a variable speed stirrer and maintained at 30° C., pH 5, was employed. For flow experiments input and output flow streams were connected by a Polystaltic metering pump (Buchler Instrument, Fort Lee, N.J.) with a sintered glass filter in the effluent line to prevent escape of the carbon-immobilized enzyme particles.

Before investigating enzyme-loaded activated carbon, several commercial carbon preparations were tested for catalytic activity for peroxide decomposition. While many exhibited high activity, large discrepancies were noted in some cases. For example, both Darco G-60 and Sigma activated charcoal powders have equal ability to separate glucose and maltose hydrate in a packed column, yet the former carbon is a relatively inactive catalyst for $H_2O_2$ decomposition. Commercial Pittsburgh activated carbon was also found to be an effective $H_2O_2$ decomposition catalyst (see FIG. 2). Because this carbon is available in a granular form better suited to possible enzyme applications, it was used as the enzyme support in all of the experiments described below.

FIG. 1 compares the deterioration from storage at 30° C. of glucoamylase and glucose oxidase activities for different immobilization methods. The solid circles represent glucoamylase immobilized on carbon by the

| | | Preparation 1 | Preparation 2 | Preparation 3 | Preparation 4 |
|---|---|---|---|---|---|
| Enzyme Loadings, Activities of Immobilized Glucoamylase and $H_2O_2$ Decomposition Activities of Activated Carbon | | | | | |
| Adsorption | Enzyme Loadings, mg/g-carbon | 42 | 45 | 43 | 2.5 |
| | Activities, $\frac{\mu \text{ mole glucose}}{\text{min. g-carbon}}$ | 8.8 | 12.2 | 14.6 | 8.7 |
| | $H_2O_2$ decomp. $t_{\frac{1}{2}}$ min. (before immobilization) | 15 min. (7 min.) | 18 min. (7 min.) | 100 min. (60 min.) | (20 min.) |
| Glutaraldehyde | Enzyme Loadings, mg/g-carbon | 35 | 42 | 44 | 7.1 |
| | Activities | 12.5 | 15.7 | 16.3 | 5.3 |
| | $H_2O_2$ decomp. $t_{\frac{1}{2}}$ min. | 80 min. | 85 min. | 200 min. | — |
| Diimide | Enzyme Loadings, mg/g-carbon | 42 | 47 | 49 | 25 |
| | Activities | 12.9 | 16.1 | 18.1 | 7.6 |
| | $H_2O_2$ decomp. $t_{\frac{1}{2}}$ | 30 min. | 45 min. | 200 min. | — |

Diimide immobilization offers improved loadings and activities for all pretreatment methods. The improvement of loading and activity obtained by a combination of nitric acid washing and diimide linkage is about 15%. It is probable that this difference will vary depending upon the particular activated carbon used.

EXAMPLE 4

Two different immobilization procedures were employed. The first, which involves enzyme adsorption followed by glutaraldehyde cross-linking, is relatively carbodiimide procedure. The open circles represent glucose oxidase immobilized by the carbodiimide procedure. The solid squares represent glucoamylase immobilized by the glutaraldehyde method of the prior art. The open triangles represent glucoamylase immobilized on carbon by adsorption only. Only the diimide preparations show negligible activity loss after 60 hours. Moreover, the diimide immobilization procedure gives very good enzyme loadings: 28 and 35 mg protein/g carbon for glucoamylase and glucose oxidase, respectively.

Even more sensitive to immobilization procedure is the peroxide-decomposing activity of the carbon-enzyme preparations. The time courses for three different batch peroxide decomposition experiments are illustrated in FIG. 2. All of these studies were conducted in a slurry reactor agitated by a marine impeller at 300 rpm.

The activated carbon with diimide linked glucoamylase was quite active for peroxide decomposition, although somewhat less active than carbon itself. This reduction of activity is likely due to covering the carbon surface hydroxyl groups, believed to be involved in catalysis of $H_2O_2$ decomposition, by the bound enzyme. Apparently the formation of a net of cross-linked glutaraldehyde over the carbon surface further obscures the carbon hydroxyl groups from peroxide in solution, causing the nearly complete loss of peroxide decomposing activity seen in FIG. 2 for the carbon with glutaraldehyde linked glucoamylase.

Based on the data in FIG. 2, it is seen that covalently linked enzymes are protected by activated carbon from peroxide deactivation, but that this beneficial action of carbon is largely lost if glutaraldehyde immobilization is used. In order to test this result further, the slurry reactor was operated with continuous addition of 500 mM $H_2O_2$ solution and simultaneous removal of the reaction mixture at the same volumetric flow rate of 5 ml/min. Periodically, a sample of carbon-immobilized enzyme particles was removed from the reactor and tested for enzyme activity.

Enzyme activity losses versus time in the continuous decomposition reactor fed with 500 mM $H_2O_2$ are plotted in FIG. 3, as are data on batch deactivation of glucose oxidase in solution in 0.2 M acetate buffer containing 500 mM $H_2O_2$. The superiority of the (diimide-coupled enzyme)-(activated carbon) preparation in resisting peroxide deactivation is clear. The 500 mM $H_2O_2$ solution used in these experiments constitutes a severe test of peroxide resistance; in previous studies of catalase as a protector against peroxide deactivation of glucose oxidase, the greatest $H_2O_2$ concentration considered was 150 mM.

We claim:

1. Method of immobilizing enzymes on activated carbon supports which comprises treating said activated carbon with a solution of an isoxazolium salt of the formula

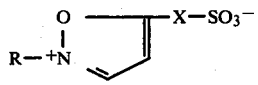

wherein R is lower alkyl and X is a bivalent lower alkylene or arylene radical, which forms a complex with reactive groups on the surface of said activated carbon, thereafter treating said activated carbon complex with a solution of an enzyme, whereby the enzyme displaces said isoxazolium salt and forms a carbon-enzyme complex, and separating said carbon-enzyme complex from the reaction media.

2. Method of claim 1 wherein the activated carbon substrate is first oxidized prior to treatment with the organic immobilizing agent.

3. Method of claim 1 wherein X is phenylene.

4. Method of claim 3 wherein R is ethyl.

* * * * *